United States Patent [19]
Reichert et al.

[11] Patent Number: 6,004,549
[45] Date of Patent: Dec. 21, 1999

[54] CRYSTALLINE PROTEIN CONTROLLED RELEASE COMPOSITIONS

[75] Inventors: Paul Reichert, Montville; Alan W. Hruza, Hackettstown; Nagamani Nagabushan; Tattanahalli Nagabhushan, both of Parsippany, all of N.J.

[73] Assignee: Schering Corporation, Kenilworth, N.J.

[21] Appl. No.: 08/355,585

[22] Filed: Dec. 14, 1994

[51] Int. Cl.$^6$ .............................. A61K 38/21; C07K 14/00
[52] U.S. Cl. ...................... 424/85.7; 424/85.4; 514/2; 514/12; 514/21; 530/351
[58] Field of Search ........................ 424/85.1, 85.4, 424/85.7; 514/2, 8, 12, 21; 530/351

[56] References Cited

U.S. PATENT DOCUMENTS

| | | | |
|---|---|---|---|
| 5,028,587 | 7/1991 | Dorschug et al. | 514/3 |
| 5,109,119 | 4/1992 | Reichert et al. | 530/402 |
| 5,157,021 | 10/1992 | Balschmidt et al. | 514/3 |
| 5,403,824 | 4/1995 | D'Souza et al. | 514/12 |
| 5,441,734 | 8/1995 | Reichert et al. | 424/85.7 |

FOREIGN PATENT DOCUMENTS 0 402 070 A1  12/1990  European Pat. Off. .
WO 94/01133   1/1994   WIPO .

OTHER PUBLICATIONS

Biosis Previews, 1978, Biosis No. 67068942, 27(4):11–16.
Benzon et al., 1987, *Anesth. Analg.* 66:553–59.
J. Anschel, 1965, *Pharm. Ind.,* 27:781–87.
List et al., 1971, Hagers Handbuch der Pharmazeutischen Praxis, Siebenter Band, Teil A., pp. 356–357.
List et al., 1985, Arzneiformenlehre, 4. Auflage, pp. 514–518.

*Primary Examiner*—Ponnathapura Achutamurthy
*Attorney, Agent, or Firm*—Jaye P. McLaughlin; Norman C. Dulak

[57] ABSTRACT

A pharmaceutical composition comprised of a crystalline protein and polyethylene glycol or vegetable oil and a process for producing the same.

23 Claims, 3 Drawing Sheets

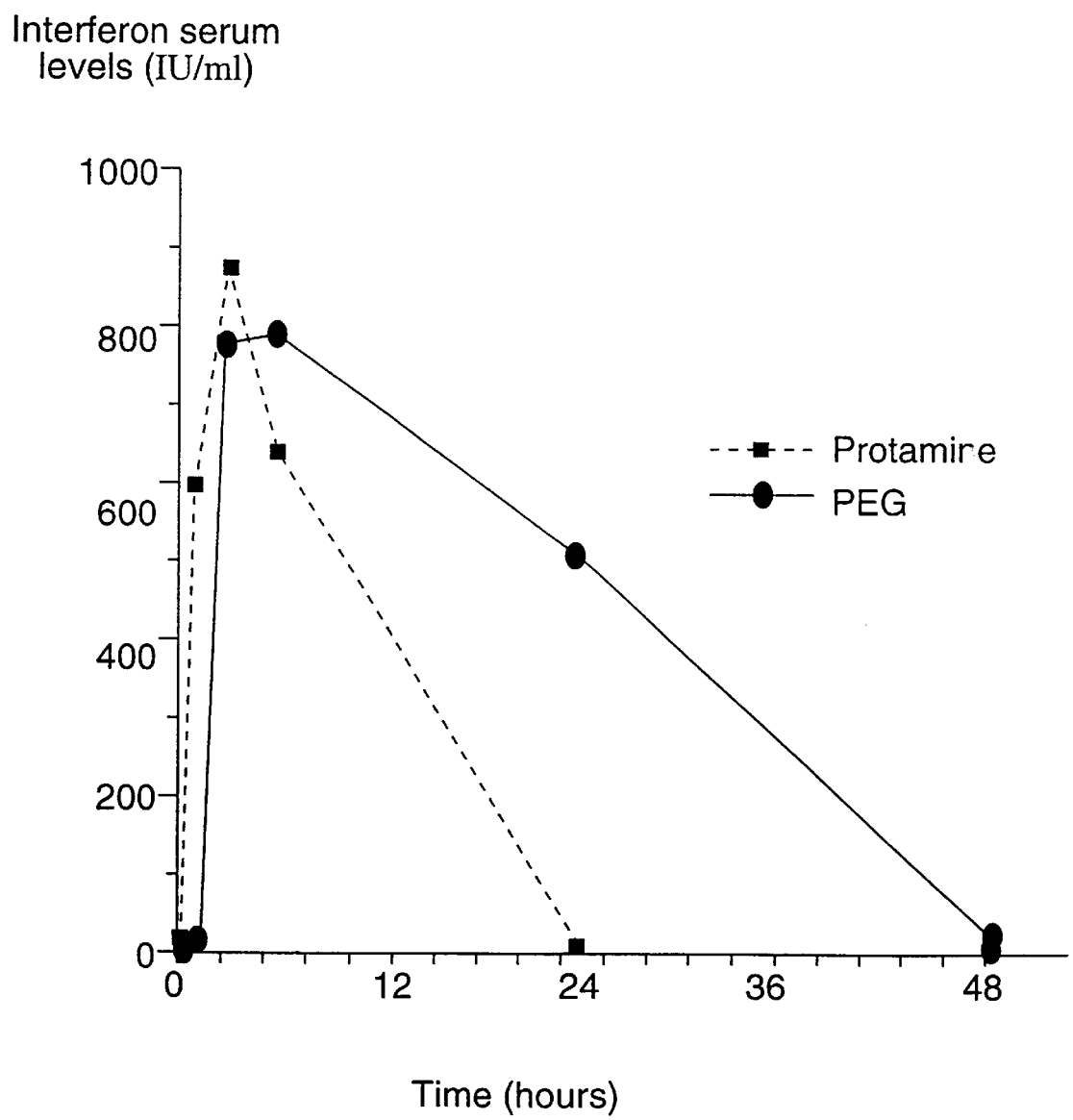

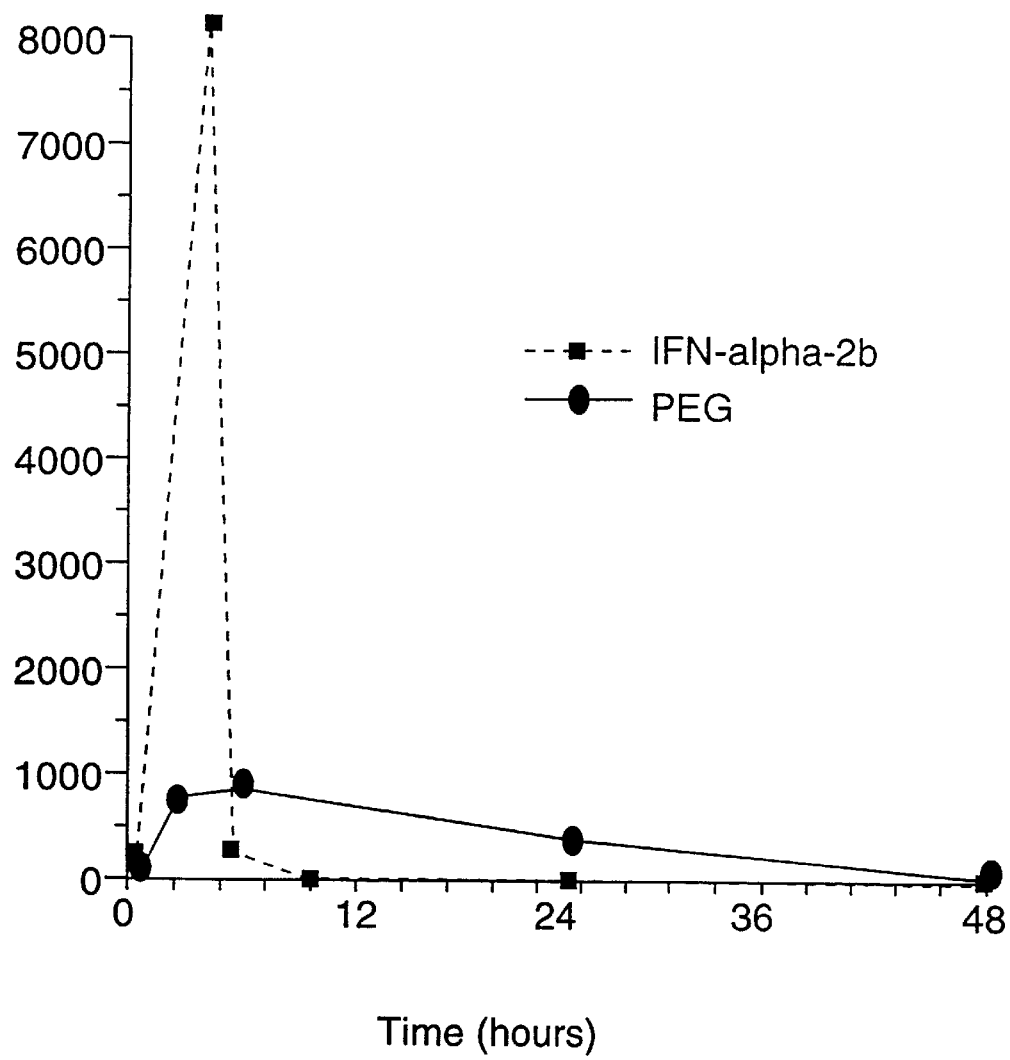

CRYSTALLINE PROTEIN CONTROLLED RELEASE COMPOSITIONS

BACKGROUND OF THE INVENTION

Proteins are frequently being used therapeutically in treating various physical conditions. Examples of such proteins are Interferon-alpha (IFN-alpha), erythropoietin (EPO), granulocyte-colony stimulating factor (G-CSF), insulin, granulocyte-macrophage-colony stimulating factor (GM-CSF) and others. Even though these proteins are useful, the dosing of these proteins is very often difficult because they have a short blood serum half-life.

For example, IFN-alpha is generally administered either by intramuscular, subcutaneous or intralesional injection usually in hospital or clinical settings. IFN-alpha has a serum half-live of 2–6 hours when injected subcutaneously or minutes when injected intravenously, and characteristically shows a "burst" or a "pulse" (i.e., a rapid blood serum level rise followed by a rapid blood serum level clearance) profile when blood levels are measured over time. Thus frequent administration of doses of the protein must be made to maintain a therapeutically effective blood serum concentration of the drug. There are clinical situations there is a need to develop an IFN-alpha formulation in which the protein is continuously released into the blood stream so that the serum concentration of the protein reaches a plateau and remains at that level for a period of time. This is known as a controlled release formulation.

Examples of pharmaceutically acceptable vegetable oils are sesame, peanut, saffron, and canola oils.

SUMMARY OF THE INVENTION

The present invention fills this need by providing for a pharmaceutical composition comprised of a mixture of a crystalline protein suspended in either polyethylene glycol or in a pharmaceutically acceptable vegetable oil.

The present invention further provides for a method of preparing a controlled release pharmaceutical composition containing containing a controlled release protein formulation comprising admixing a crystalline protein with either polyethylene glycol or with a pharmaceutically acceptable vegetable oil.

The present invention provides still further a method of administering a crystalline protein to an individual comprising mixing the crystalline protein in either polyethylene glycol or a pharmaceutically acceptable vegetable oil, and injecting the mixture into the individual.

BRIEF DESCRIPTION OF THE DRAWING

FIG. 2 depicts a comparison of serum levels of IFN alpha-2b in which crystalline zinc IFN alpha-2b was administered either in a Protamine vehicle or a PEG vehicle.

FIG. 3 depicts a comparison of serum levels crystalline zinc IFN alpha-2b in a PEG vehicle vs non-crystalline IFN alpha-2b in a phosphate buffered solution which were administered to cynomolgus monkeys as determined by a CPE assay.

DETAILED DESCRIPTION OF THE INVENTION

Figure 1:
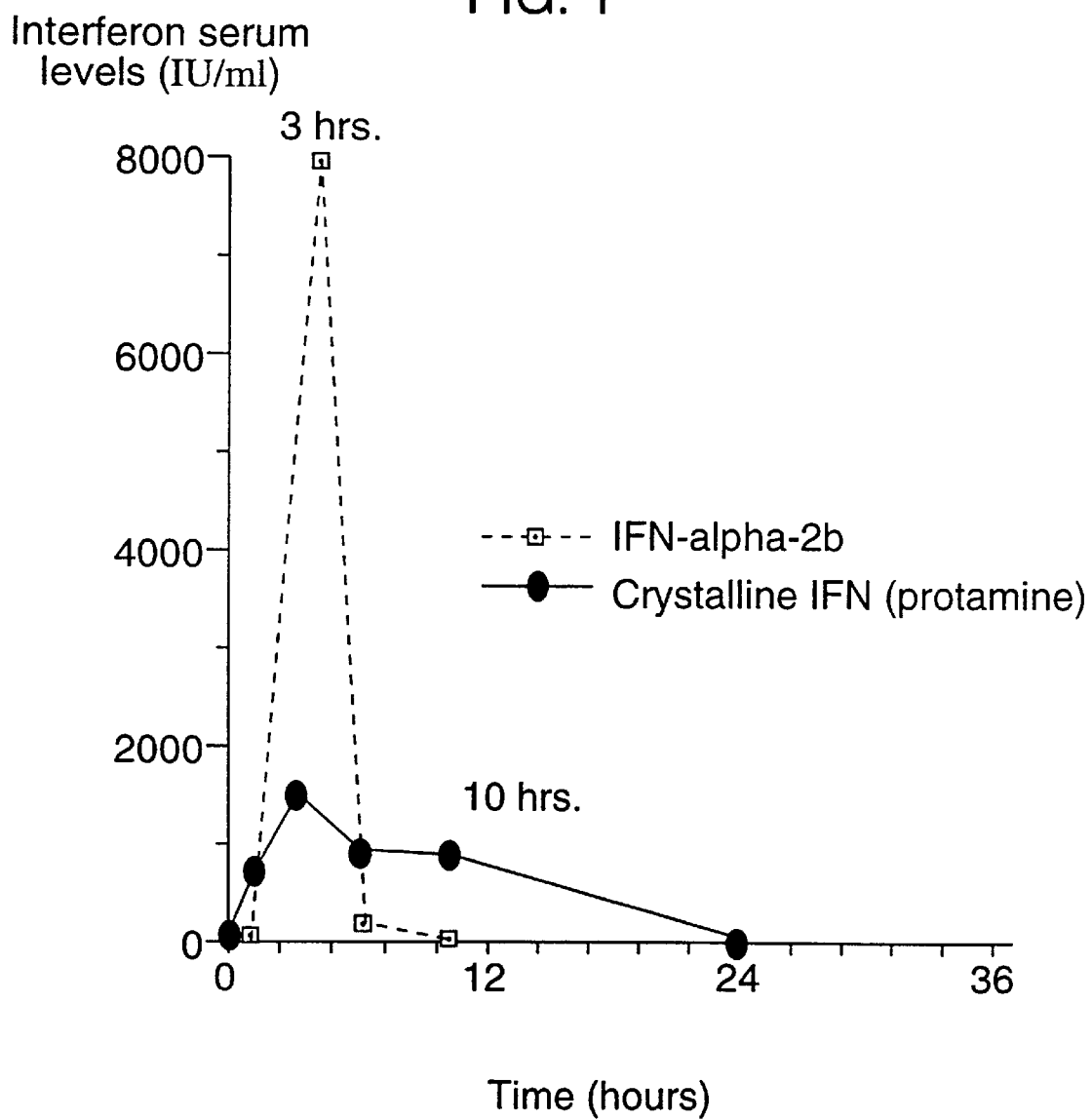
FIG. 1 depicts serum blood level of Interferon alpha-2b in phosphate buffer solution, graph 10, and of crystalline zinc interferon alpha-2b as a function of time injected by means of a protamine sulfate vehicle, graph 12.

The present invention relates to pharmaceutical compositions comprised of a crystalline protein and polyethylene glycol or a pharmaceutically acceptable vegetable oil such as sesame, peanut, saffron and canola oils.

Polyethylene glycols (α-hydroxy-ω-hydroxy poly (oxy-1,2-ethanedidyl) (PEGs) are a family of linear polymers formed by the addition reaction of ethylene oxide. The generalized formula for polyethylene glycol is:

HO—(CH$_2$CH$_2$O)n-H, where "n" is the average number of repeating oxyethylene groups. The repeating ether linkages and terminal hydroxyl give rise to the water solubility of PEGs. In general, each PEG is followed by a number which corresponds to its average molecular weight. For example, polyethylene glycol 400 has an average value of n between 8.2 and 9.1 and a molecular weight range of 380 to 420 and is a liquid at 22° C. Whereas polyethylene glycol 6000 has an n value of between 158 and 204 and has a molecular weight range 7000–9000. PEG 6000 is a powder or is comprised of creamy white flakes at 22° C.

Polyethylene glycol polymers have been used in protein crystallization studies. The differential solubility of proteins in polyethylene glycol solutions has been utilized in the course of purification and crystallization studies. The use of polyethylene glycol has been well documented as a precipitant to induce growth of protein crystals suitable for X-ray diffraction studies.

PEGs in general have been found to be well tolerated and are believed to have a relatively low level of toxicity. There are currently numerous governmental approved injectable solution formulations where PEGs are used for vehicles. The metabolic fate of PEGs is known, they have been found to be secreted intact in the urine within hours post injection. However, a pharmaceutical composition comprised of a mixture of a crystalline protein and a PEG has not heretofor been disclosed. This composition results in a protein formulation having unexpectantly high controlled release properties.

To prepare a PEG/crystalline protein mixture according to the present invention, one must choose a PEG having a suitable molecular weight which can be placed in solution or a gel, or is already in a liquid or gel form. Generally, a viscous PEG solution or gel is preferred. However, the PEG solution or gel must be fluid enough to freely flow through the needle of a tuberculin syringe when ejected. Examples of suitable PEG preparations are the following: a 40% aqueous solution of PEG 8000, a 50% solution of PEG 3350, a mixture of PEG 40,000 and PEG 550, a mixture of PEG 3350 and PEG 300, and a mixture of PEG 3350 and PEG 400.

If a solution of a solid PEG such as of PEG 8000 is used, the appropriate amount of PEG is measured out and dissolved in water generally with stirring at ambient temperature of about 22° C, pH 5–7, preferably pH 6.1. The PEG solution is then filtered generally through a 0.2 μm (μm) filtration unit.

If a high molecular weight PEG such as PEG 40,000 is mixed with a low molecular weight PEG, generally the high molecular weight PEG is placed in a vesicle and is heated until it liquefies. Into the liquefied PEG is stirred the lower molecular weight PEG such as PEG 550. The mixture is then filtered generally through a 0.2 μ filter.

The crystalline protein is then measured out to the concentration desired as determined by standard protein assay as for example the Bradford assay. The crystals are centrifuged, the supernatant removed and the crystal are washed and centrifuged again. The supernatant is removed and the resultant pellet is resuspended into the PEG formulation with mixing, generally by vortexing. This results in a uniform crystalline suspension.

A crystalline protein can also be administered according to the present invention in a vegetable oil vehicle. In this embodiment a crystalline protein is prepared as described above and simply mixed with a pharmaceutical grade of a pharmaceutically acceptable vegetable oil. Examples of acceptable vegetable oils are peanut, sesame, saffron and canola oils forming an emulsion. In another embodiment, a gel is formed by the addition of aluminum monosterate to the vegetable as described below.

The present invention lies in the fact that when crystalline proteins suspended in a PEG solution or gel, or in a vegetable are administered to an individual they exhibit unexpectantly high controlled release effects. That is the length of time that the protein is present in the blood serum is dramatically increased.

EXAMPLES

The following examples are included to illustrate but not to limit the present invention.

The IFN-alpha-2 employed in the following examples was recombinant human interferon alpha-2b expressed in *E. coli* as described in Weissmann, et al. *Science,* 209:1342 (1980). The cells were cultured, harvested and extracted as previously reported in Leibowitz, P. et al., U.S. Pat. No. 4,315,852. The resulting extract was purified by a combination of conventional purification steps: ethanol extraction, matrix gel blue ligand affinity chromatography, ion exchange and gel filtration chromatography. The resulting purified IFN-alpha-2b preparation was dialyzed against either USP grade water or 0.1% trifluoroacetic acid solution and lyophilized as either the free base or trifluoroacetate salt respectively.

Example 1

Production of Crystalline Zinc IFN-alpha-2b having a Monoclinic Morphology

Using an automated crystallization system as disclosed in Kenyon et al., U.S. patent application Ser. No. 07/822,504 filed Jan. 17, 1992, International Patent Application No. PCT/US92/08296 filed Oct. 6, 1992, 6 μl droplets containing 20 mg/ml of IFN-alpha-2b in 17 mM sodium acetate, 17 mM zinc acetate, pH 5.5 were hung from the upper cover of a siliconized crystallization chamber. The upper plate was placed on the greased lower assembly of the crystallization chamber over a well containing 1 ml of 35 mM sodium acetate, 35 mM zinc acetate, pH 5.5. Large monoclinic crystals were evident from 5–6 days after incubation at 22° C.

Example 2

Production of Crystalline Zinc IFN-alpha-2b having a Monoclinic Morphology

In an alternative procedure, crystalline zinc IFN-alpha-2b having monoclinic morphology was produced. In this procedure, the zinc IFN-alpha-2b crystallization condition consisted of a 10 μl droplet containing 20 mg/ml IFN-alpha-2b in 2.5 mM sodium acetate, 37.5 mM zinc acetate, pH 6.1 hung from an 18 mm circular siliconized cover slide. The crystallization chamber containing 1 ml of 5 mM sodium acetate, 75 mM zinc acetate, pH 6.1, was sealed to the siliconized cover slide by a bead of high vacuum grease around the rim of the crystallization chamber, thus suspending the hanging droplet above the crystallization chamber and above the acetate salt solution. Large monoclinic crystals were produced within 5–6 days after incubation at 12° C.

Example 3

Production of Crystalline Zinc IFN-alpha-2b having a Monoclinic Morphology

In an alternative procedure, crystalline zinc IFN-alpha-2b having monoclinic morphology was produced. In this procedure, a 10 μl drop containing 20 mg/ml IFN-alpha-2b in 45 mM zinc acetate, pH 6.1 was suspended from the siliconized cover slide. The crystallization chamber contained 1 ml of 90 mM zinc acetate, pH 6.1 and was sealed with high vacuum grease to the cover slide suspending the hanging droplet above the crystallization chamber and above the zinc acetate solution. Large monoclinic crystals were produced within 5–6 days after incubation at 12° C.

Example 4

X-Ray Diffraction Data of Monoclinic IFN-alpha 2b

For X-ray studies, IFN-alpha-2b monoclinic crystals produced according to the process of Example 1 were mounted in glass capillaries at 22° C. using CuKα radiation from a Rigaku RU-300 rotating anode generator operating at 40 kV and 100 mA. The native data set was collected on a Nicolet X-100A area detector using the same radiation source.

The crystals were stable to X-ray diffraction analysis and diffracted to about $2.7\times10^{-10}$m (Å) resolution, but the data became much weaker at about $3.2\times10^{-10}$m (Å) resolution. Different batches of crystals were subjected to X-ray analysis and gave consistent results with respect to morphology. The crystals index in space group $P2_1$ with cell parameters $a=63.1\times10^{-10}$m (Å), $b=76.6\times10^{-10}$m(Å), $c=151.4\times10^{-10}$m (Å), $\alpha=90°$, $\beta=91.2°$and $\gamma=90°$. This is the first report of a metal alpha interferon having a monoclinic morphology.

Example 5

Liquid Diffusion Crystallization Method (Plates)

In order for a crystalline suspension to have utility in a controlled release application, it must be possible to manufacture crystals in the milligram to gram scale. The current vapor diffusion in hanging drop method is not applicable to crystallize proteins at this scale. Experiments were set up to crystallize IFN-alpha-2 using a bulk dialysis method which mimicked the vapor diffusion in hanging drop method. A 0.5 ml solution of IFN-alpha-2b (40 mg/ml), 35 mM sodium acetate, pH 5.5 was dialyzed using a microdialysis bag having a molecular weight cutoff of 5000 kD (Pope Scientific Inc., Menomonee Falls, Wis.) against 2.7 liters of 35 mM sodium acetate, pH 5.5 at 22° C. A zinc acetate solution (0.3M) buffered to pH 5.5 was added dropwise over a two day period at 22° C. The purpose of dropwise addition was to slowly raise the zinc acetate level to 35 mM in the IFN-alpha-2b solution. A precipitate in suspension was observed after 1–2 hours of zinc acetate solution addition. The suspension was monitored microscopically daily. After 2 weeks, a few plates were observed in the suspension. The number of plates in the suspension increased daily (average size; 70 μm) until the suspension contained about 90% crystals after 3 weeks.

Example 6

Liquid-diffusion Crystallization Method (Plates)

A 0.5 ml IFN-alpha-2b solution having a concentration of 40 mg/ml of IFN-alpha-2b in 35 mM sodium acetate, pH 5.5 was dialyzed using a microdialysis bag having a molecular weight cutoff of 5000 kD (Pope Scientific Inc., Menomonee Falls, Wis.) against 2.7 liters of a buffer solution comprised of 35 mM sodium acetate and 35 mM zinc acetate, pH 5.5. The resulting suspension was incubated at 22° C. for 3 weeks. Masses of plate crystals were evident from 3–4 weeks by microscopic inspection.

Example 7

Temperature Induction Crystallization Method (Plates)

A 0.5 ml IFN-alpha-2b solution having a concentration of 40 mg/ml of IFN-alpha-2b in 35 mM sodium acetate, 35 mM zinc acetate pH 5.0 was adjusted to pH 6.0 using 1 M sodium hydroxide at 4° C. The resulting suspension was submerged in a refrigerated bath/circulator (model #RTE-110, Neslab Instruments, Inc., Newington, N.H.). The temperature of the water bath was increased to 22° C. using a linear gradient over 4 days. Masses of plate crystals were evident after 4 days by microscopic inspection.

Example 8

Production of Crystalline Zinc IFN-alpha-2b Using a Combination of Vapor Diffusion and Temperature Induction Methods Using a combination of vapor diffusion and temperature induction, crystalline zinc IFN-alpha-2b having monoclinic morphology was produced. In this procedure, a 10 gl droplet containing 20 mg/ml IFN-alpha-2b in 40 mM zinc acetate, pH 6.0 was suspended from a siliconized cover slide at 4° C. The crystallization chamber contained 1 ml of 80 mM zinc acetate, pH 6.0 and was sealed with high vacuum grease to the coverslide suspending the hanging droplet above the crystallization chamber. The entire chamber was transferred to an incubator in which the temperature was 12° C. Large monoclinic crystals were produced within 3–5 days after incubation at 12° C.

Example 9

Preparation of Crystalline Zinc IFN α-2b Using a Temperature Induction Method Forty (40) mg of lyophilized interferon alpha-2b was weighed out and rehydrated in 1 ml of USP grade water and filtered using a $0.2\mu$ filter. The solution was dialyzed in a 10,000 Dalton molecular weight cut off dialysis bag (Pope) against 90 mM zinc acetate, pH 5.0 for 18 hours at 4° C., after which the solution was redialyzed in a 10,000 Dalton molecular weight cut off dialysis bag (Pope) against 90 mM zinc acetate, pH 6.0 for 18 hours at 4° C. The solution was then transferred to a sterile glass vial and the temperature was increased from 4–14° C. for 18 hours. At which time, masses of monoclinic crystals (53×55×80 $\mu$m) were observed.

Examples 10–15

Characterization

Studies were initiated to characterize the zinc IFN-alpha-2b crystals using physical biochemical methods to insure molecular integrity, protein zinc content and retention of biological activity after dissolution.

Example 10

Protein Assay

An aliquot of bulk zinc IFN-alpha-2b crystals produced by the procedure of Example 3 was dialyzed against 2 liters of 35 mM sodium acetate, pH 5.5 at 22° C. for 4 days to remove non-complexed zinc acetate. The suspension was centrifuged and the wash solution was removed with a Pasteur pipette. The washed crystals were redissolved in 8 M guanidine hydrochloride solution at 22° C. Protein concentration was determined by a modified Bradford assay using pure human IFN-alpha-2b as a reference standard. Bradford assay: A modification of the standard Coomassie blue dye binding assay so that the absorbance is directly proportional to protein concentration. Details are in Bradford, M., *Anal. Biochem.* 72:248 (1976).

Example 11

HPLC

Analytical high performance liquid chromatography (HPLC) (Waters Ass., Milford, Mass.) was performed on an aliquot of redissolved IFN-alpha-2b crystals produced according to the procedure of Example 3. The sample was applied to a RAININ DYNAMAX® $C_4$ 300×10$^{-10}$m (Å) column (4.6×250 mm) which was subsequently eluted with a linear gradient of acetonitrile 27–72% in 0.1% trifluoroacetic acid over a 30 minute period. A Gilson variable wavelength detector set at 280 nm with a sensitivity of 0.02 absorbance units was used to monitor the eluate. The retention times and chromatographic profiles of both the redissolved crystal solution and the original IFN-alpha-2b preparation prior to crystallization were indistinguishable.

Example 12

SDS-PAGE Analysis

Crystals harvested from a vapor diffusion in hanging drop experiment according to the procedure of Example 1 were centrifuged and washed several times to remove any soluble IFN-alpha. The centrifuged pellet was dissolved in a buffer containing sodium dodecyl sulfate. The resulting solution was run on a 12% sodium dodecyl sulfate-polyacrylamide gel electrophoresis (SDS-PAGE), Laemmli, U.K. *Nature*, 227:680 (1970) vs. a sample of IFN-alpha-2b. There was no apparent change in the molecular weight of the dissolved crystals vs. the control IFN-alpha-2b samples. Based on these results, there was no evidence of chemical or enzymatic modification of the IFN-alpha-2b during the crystallization process or subsequent dissolution.

From the results of Examples 10 and 11 above, it can be concluded that no chemical changes or any denaturing of the protein took place during the crystallization or reconstitution.

Example 13

Physical Properties of Zinc IFN-alpha 2b

The properties of the crystals produced according to the procedure of Example 1 were probed for suitability in controlled release formulations by observing microscopically their stability at 37° C. (body temperature) and 4° C. Also, crystal stability was observed in a non-zinc buffer at different pH's over a period of 18 hours. The crystals were found to be stable for 24 hours at 37° C. and 4° C. and stable between pH 5.0–6.0. This differs from the characteristics of the previous crystalline IFN-alpha-2b preparations, especially the crystals from Nagabhushan, et al., 'Characterization of genetically Engineered alpha-2 interferon', In: *Interferon: Research, Clinical Application and Regulatory*, which dissolve readily above and below pH 6.0 as well as at 4° C. at pH 6.0.

Example 14

Molar Ratio of Complexed Zinc vs. Interferon Content

An experiment was designed to determine the molar ratio of complexed zinc vs. IFN-alpha-2b. An aliquot of bulk zinc-IFN-alpha-2b crystals produced according to the procedure of Example 3 was dialyzed against 2 liters of 35 mM sodium acetate, pH 5.5 for 4 days to remove non-complexed zinc acetate. An 8.0 M guanidine hydrochloride solution was added to the washed suspension to dissolve the complex. The resulting solution was assayed using a Bradford assay for protein content. A sample of the same suspension was submitted for a zinc assay based on atomic absorption analysis. A 3.1 to 1 molar ratio of zinc ions to IFN-alpha-2b was found. Analysis of subsequent batches of zinc-IFN-alpha-2b gave a ratio of from 2 to 4 moles of zinc ions per mole of IFN-alpha-2b.

Example 15

Cytopathic Effect Inhibition Assay

To determine if the crystalline IFN-alpha-2b retained its biological activity a cytopathic effect inhibition assay was carried out. The virus which was used was the Encephalomyocarditis virus (EMC), ATCC strain VR-129B, and was grown in monolayer cultures of Vero cells and stored frozen in Medium A. (Medium A is comprised of 950 ml of Minimum Essential Medium Eagle with Earle's balanced salt solution (Gibco Inc.), 100 ml fetal bovine serum, 36 ml of 7.5% sodium bicarbonate, 20 ml of 1M HEPES Buffer in saline, 20 ml of 200 mM L-Glutamine, and 10 ml of penicillin and streptomycin (10,000 unit of K-Penicillin/ml. and 10,000 μg streptomycin sulfate/ml).

Confluent monolayers of FS-71 cells in tissue culture roller bottles were rinsed with Hank's balance salt solution and incubated at 37° C. for 10 minutes with a 2.5% trypsin solution. The trypsin solution containing the cells was diluted in Medium A such that the concentration of cells was $3.5 \times 10^5$ and used in the assay as described below.

Interferon Assay: The entire procedure for the anti-viral Bioassay was done in a 96 well microtiter plate. The samples to be tested were placed into the appropriate wells and serially diluted 1:2 across the plate. On each plate, 24 wells were filled with Medium A to serve as virus and cell controls. Additionally, a laboratory standard of interferon alpha-2b containing 600 IU/ml of Interferon alpha-2b was diluted to 1 IU/ml, the concentration level necessary to give a 50% protection level from viral cytopathology, was included in all assays so that the relative anti-viral activity of samples could be determined and compared across assays.

Each well was then seeded with approximately $3.5 \times 10^4$ cells in 0.1 ml of Medium A. The plate was covered and incubated at 37° C., 5% $CO_2$ for 4 hours. All wells, except the cell control wells, received EMC virus at a concentration appropriate to induce 90–100% cytopathology in 16–18 hours post-infection which was approximately $1.54 \times 10^4$ plaque forming units. The plates were recovered and incubated at 37° C., 5% $CO_2$ until the virus control wells displayed a cytopathic effect (CPE) of at least 90%.

The media from each well was aspirated and the cell monolayer was strained with 0.1 ml crystal violet preparation for about 30 minutes. After the crystal violet was decanted, the plates were gently rinsed with water and allowed to air dry. The virus and cell control wells were scored from 1 to 4+ (1=<10% CPE and 4=>90% CPE) by visual inspection of the monolayer with and without a microscope. Samples on test plates that showed appropriate control responses were then graded.

The grading of each sample well consisted of visual examination and comparison by the standard wells. The 50% endpoint for samples are determined by direct comparison to the 50% endpoint for the standard by selection of the sample well(s) which match most closely. The shift in a sample's 50% endpoint as compared to that of the standard gives estimates of titer values relative to the standard. Therefore, a shift of X wells [X=(50% well No. for sample)–(50% well No. for standard)] translates to a potency of $2^x$ times the potency of the standard. A detailed description of the assay is provided in S. Rubinstein, P. C. Familetti and S. Petska, *J. Virol.* 37:755 (1981).

Example 16

Controlled Release Potential of Zinc-Interferon alpha 2b in a Protamine Vehicle.

An in vivo experiment was devised to test the controlled release potential of the crystalline suspension in a GRAS formulation suitable for subcutaneous injection. Using IFN-alpha-2b produced according to the procedure of Example 7, a sterile zinc-IFN-alpha-2b crystalline suspension ($34 \times 10^6$ IU/dose) was prepared in 10 mM sodium acetate, 10 mM zinc acetate, 0.4 mM protamine sulfate, pH 5.5 buffer. This suspension was injected subcutaneously into the small of the back of two Cynomolgus monkeys. The interferon blood serum level was monitored as a function of time at 1, 3, 6, 10, 24, 48 and 72 hours using the cytopathic effect inhibition assay (CPE).

See graph 12 of FIG. 1 which shows the IFN-alpha mean serum level of the two monkeys determined by the CPE assay as a function of time.

Example 17

Control Study

The experimental results obtained in Example 15 differ from the present experiment in which non-crystalline IFN-alpha-2b was prepared in a normal saline phosphate buffer solution. A Cynomolgus monkey received a subcutaneous injection in the small of the back at a dosage of $50 \times 10^6$ IU/injection. The interferon levels in the blood serum were measured at 0, 1, 3, 6, 10, 24, 48, and 72 hours. The data are shown graphically in graph 10 of FIG. 1 which shows the IFN-alpha serum level as determined by the CPE assay as a function of time.

From Examples 17 and 18, it can be concluded that the use of crystalline zinc IFN-alpha in a protamine vehicle results in a prolonged detectable level of IFN-alpha in the blood serum relative to the prior art IFN-alpha administration described in Example 16. Furthermore, the data supports the utility of zinc interferon crystalline suspension as a controlled release formulation. The crystalline complex can be manufactured in large quantities using a process based on bulk dialysis or temperature induction. This large scale process produces crystals in the 1–200 μm size which is desirable for an injectable product (can be injected with a tuberculin syringe).

TABLE 1

Pharmacokinetic Profile for Crystalline IFN Suspension vs. Non-Crystalline IFN in Monkeys

|  |  | FIG. 1 Graph 10 | FIG. 1 Graph 12 |
|---|---|---|---|
| Cmax |  | 8000 | 1500 |
| Tmax |  | 3 | 3 |
| AUC (tf) |  | 20225 | 16812 |
| tf |  | 6 | 24 |
| Cmax | IU/ml | Maximum plasma concentration | |
| Tmax | hr. | Time of maximum plasma concentration | |
| AUC (tf) | IU · hr/ml | Area under the plasma concentration-time curve from the time 0 to time of final measurable sample | |
| tf | hr | Time of final measurable sample | |

TABLE 2

Serum Level (CPE) vs. Time

| Time (hr) | FIG. 1 Graph 10 | FIG. 1 Graph 12 (mean) |
|---|---|---|
| 0 | 0 | 0 |
| 1 | 0 | 676 |
| 3 | 8000 | 1500 |
| 6 | 150 | 900 |
| 10 | 0 | 114 |
| 24 | 0 | 0 |
| 48 | 0 | 0 |
| 72 | 0 | 0 |

Example 18

Cobalt-Interferon alpha-2b Complex Crystals

Using an automated crystallization system as disclosed in Kenyon et al., U.S. patent application Ser. No. 07/822,504 filed Jan. 17, 1992, International Patent Application No. PCT/US92/08296 filed Oct. 6, 1992, a 6 μl droplet containing 20 mg/ml of alpha-2b interferon in 17 mM sodium acetate, 22 mM cobalt acetate, pH 4.6 was hung from the upper cover of a siliconized crystallization chamber. The upper plate was placed on the greased lower assembly of the crystallization chamber over a well containing 1 ml of 35 mM sodium acetate, 45 mM cobalt acetate, pH 4.6. Crystals were evident from 5–6 days after incubation at 22° upon microscopic inspection.

Example 19

Production of Crystalline Zinc IFN-alpha-2b using Lithium Acetate in the Crystallization Buffer A 10 μl droplet containing 20 mg/ml IFN-alpha-2b in 37.5 mM zinc acetate, pH 6.1, 2.5 mM lithium acetate was suspended from the underside of a siliconized cover slide. The crystallization chamber contained 1 ml of 75 mM zinc acetate, pH 6.1, 5.0 mM lithium acetate and was sealed to the coverslide with high vacuum grease. Monoclinic crystals appeared in 5–6 days after incubation at 12° C.

Example 20

Production of Crystalline Zinc IFN-alpha-2b using Potassium Acetate in the Crystallization Buffer A 10 μl droplet containing 20 mg/ml IFN-alpha-2b in 37.5 mM zinc acetate, pH 6.1, 2.5 mM potassium acetate was suspended from the underside of a siliconized cover slide. The crystallization chamber contained 1 ml of 75 mM zinc acetate, pH 6.1, 5.0 mM potassium acetate and was sealed to the coverslide with high vacuum grease. Large monoclinic crystals appeared in 5–6 days after incubation at 12° C.

Example 21

Preparation of Crystalline Zinc IFN-alpha-2b Using a Temperature Induction Method Eighty (80) mg of lyophilized interferon alpha-2b was weighed out and rehydrate in 2 ml of USP grade water, and filtered using a 0.2μ filter. The solution was dialyzed in a dialysis bag having a 10,000 Dalton molecular weight cut-off (Pope) against 35 mM sodium acetate, 35 mM zinc acetate, pH 5.0 for 18 hours at 4° C., after which the solution was redialyzed in (Pope) dialysis bag against 35 mM sodium acetate, 35 mM zinc acetate, pH 6.1 for 18 hours at 4° C. The solution was then transferred to a sterile vial ramp temperature to 22° C. for 5 days. At which time masses of plate crystals (35×60×0.5 μm) appeared.

Example 22–39

Examples 22–39 show the preparation of controlled release crystalline protein preparations in a polyethylene glycol vehicle

Example 22

Preparation of 10 mM sodium acetate, 10 mM zinc acetate. pH 6.1, 40% PEG 8000 solution A controlled release formulation of crystalline zinc IFN-alpha-2b was formed in the following manner.

Into 600 ml of USP grade water was dissolve 1.35 g of sodium acetate (Fisher) and 2.19 g. of zinc acetate (Fisher). Into the solution was added 400 g of PEG 8000 (Union Carbide) with stirring until in solution. Glacial acetic acid (reagent grade, Fisher) was then added dropwise until pH 6.1@ 22° C. to the stirring solution. The solution was then filtered in a laminar flow hood using a Nalgene sterile 0.2 μm filtration unit (1 liter capacity).

Preparation of Crystalline Zinc Human-IFN-alpha-2b Formulations

Preparation of Crystalline interferon suspension in 10 mM sodium acetate, 10 mM zinc acetate, pH 6.1.40% PEG 8000

Into a microcentrifuge tube was placed 15 μl of crystalline zinc IFN-alpha-2b suspension containing 100×10⁶ IU/ml and centrifuged in a Beckman microfuge II at 1000 rpm for 5 minutes. The supernatant liquid was decanted off and the resultant pellet of crystalline zinc IFN-alpha was resuspended in 1 ml of 35 mM sodium acetate, 35 mM zinc acetate, pH 6.1. This suspension was then centrifuged in a Beckman microfuge II at 1000 rpm for 5 minutes; and the supernatant liquid was decanted off. The resulting pellet was resuspended in 2 ml of 0.2 μm filtered 10 mM sodium acetate, 10 mM zinc acetate, pH 6.1, 40% PEG 8000. The resulting suspension was then vortexed on an orbital shaker until a uniform suspension containing 50×10⁶ IU/ml of crystalline zinc IFN-alpha-2b in a polyethylene glycol vehicle was obtained. This mixture was stored at 22° C. until it was used.

Example 23

Preparation of 10 mM sodium acetate, 10 mM zinc acetate, pH 6.1, 50% PEG 3350 solution Into 500 ml of USP grade water were dissolve 1.35 g of sodium acetate (Fisher) and 2.19 g of zinc acetate (Fisher).

Into the solution were added 500 g of PEG 3350 (Union Carbide) with stirring until in solution. Glacial acetic acid (reagent grade, Fisher) was added dropwise into the stirred solution until the solution obtained pH 6.1 @ at 22° C. The solution was filtered in a laminar flow hood using a Nalgene sterile 0.2 μm filtration unit (1 liter capacity).

Preparation of Crystalline interferon suspension in 10 mM sodium acetate, 10 mM zinc acetate, pH 6.1. 50% PEG 3350

Into a microcentrifuge tube was placed 15 μl of crystalline zinc IFN-alpha-2b suspension containing 100×10$^6$ IU/ml and centrifuged in a Beckman microfuge II at 1000 rpm for 5 minutes. The supernatant liquid was decanted off and the resultant pellet was resuspended in 1 ml of 35 mM sodium acetate, 35 mM zinc acetate, pH 6.1. This suspension was then centrifuged in a Beckman microfuge II at 1000 rpm for 5 minutes. The supernatant liquid was decanted off and the resulting pellet was resuspended in 2 ml of 0.2 μm filtered 10 mM sodium acetate, 10 mM zinc acetate, pH 6.1, 50 % PEG 3350. The resulting suspension was then vortexed on a orbital shaker until a uniform suspension containing 50×10$^6$ IU/ml of crystalline zinc IFN-alpha-2b in a polyethylene glycol vehicle was obtained. This mixture was stored at 22° C. until used.

Example 24

Preparation of PEG 40,000/550 gel

Into a beaker was placed 1 g of PEG 40,000 (Serva Corporation) and heated until it became a liquid at approximately 80° C. Into the liquefied PEG 40,000 were added 4.1 ml of PEG 550 (Aldrich Chemical Co.) with stirring until a uniform solution was obtained. The warm PEG mixture was filtered under sterile conditions in a laminar flow hood. The resulting mixture was allowed to cool to 22° C. to form a gel.

Preparation of Crystalline IFN-alpha-2b suspension in PEG 40,000/550 gel

Into a microcentrifuge tube were placed 15 μl of crystalline zinc IFN-alpha-2b suspension containing 100×10$^6$ IU/ml of crystalline zinc IFN-alpha-2b and centrifuged in a Beckman microfuge II at 1000 rpm for 5 minutes. The supernatant liquid was decanted off and the resultant pellet was resuspended in 1 ml of 35 mM sodium acetate, 35 mM zinc acetate, pH 6.1. The resultant suspension was then centrifuged in a Beckman microfuge II at 1000 rpm for 5 minutes. The supernatant liquid was then decanted off. The resulting pellet was then blended in 2 ml of 0.2 μm filtered PEG 40,000/550 gel. Using a spatula the mixture was blended in a laminar flow hood to a uniform suspension containing 50×10$^6$ IU/ml of zinc IFN-alpha-2b. The resultant mixture was then stored at 22° C. until used.

Example 25

Preparation of PEG 3350/300 gel

Into a beaker were placed 8 g of PEG 3350 (Union Carbide) until it turned to liquid at approximately 80° C. To the liquefied PEG 3350 were added 32 ml of PEG 300 (Union Carbide) with stirring until uniform solution was obtained. The resultant warm PEG mixture was filtered using a 0.2μ filter under sterile conditions in a laminar flow hood. The resulting mixture was cooled to 22° C. to form a gel.

Preparation of Crystalline IFN suspension in PEG 3350/300 gel

Into a microcentrifuge tube were placed 15 μl of crystalline zinc IFN-alpha-2b suspension containing 100×10$^6$ IU/ml of crystalline zinc IFN-alpha-2b and centrifuged in a Beckman microfuge II at 1000 rpm for 5 minutes. The supernatant liquid was decanted off, and the resultant pellet was resuspended in 1 ml of 35 mM sodium acetate, 35 mM zinc acetate, pH 6.1. This suspension was then centrifuged in a Beckman microfuge II at 1000 rpm for 5 minutes. The supernatant liquid was decanted off. The resulting pellet was then blended in 2 ml of 0.2 μm filtered PEG 40,000/550 gel. Using a spatula the mixture was blended in a laminar flow hood to a uniform suspension containing 50×10$^6$ IU/ml of zinc IFN-alpha-2b. The resultant mixture was then stored at 22° C. until used.

Example 26

Preparation of PEG 3350/400 gel

Into a beaker were placed 6 g of PEG 3350 (Union Carbide) and heated until it turned into a liquid at approximately 80° C. To the liquefied PEG were added 34 ml of PEG 400 (Union Carbide) with stirring until a uniform solution was obtained. The warm PEG mixture was filtered using a 0.2 μm filter under sterile conditions in a laminar flow hood. The resulting mixture was cooled to 22° C. to form a gel.

Preparation of Crystalline IFN suspension in PEG 3350/400 gel

Into a microcentrifuge tube were placed 15 μl of crystalline zinc IFN-alpha-2b suspension containing 100×10$^6$ IU/ml of crystalline zinc IFN-alpha-2b and centrifuged in a Beckman microfuge II at 1000 rpm for 5 minutes. The supernatant liquid was decanted off, and the resultant pellet was resuspended in 1 ml of 35 mM sodium acetate, 35 mM zinc acetate, pH 6.1. The suspension was centrifuged in a Beckman microfuge II at 1000 rpm for 5 minutes. The supernatant liquid was decanted off, and the resulting pellet was blended in 2 ml of 0.2 μm filtered PEG 3350/400 gel. Using a spatula the mixture was blended in a laminar flow hood to a uniform suspension containing 50×10$^6$ IU/ml of zinc IFN-alpha-2b. The resultant mixture was then stored at 22° C. until used.

Example 27

Preparation of Crystalline human insulin suspension in 10 mM sodium acetate, 10 mM zinc acetate, pH 6.1, 40% PEG 8000

Into a microcentrifuge tube was placed 1.0 ml of HUMULIN® U (Lilly) containing 100 units/ml of crystalline insulin and centrifuged in a Beckman microfuge II at 1000 rpm for 5 minutes. The supernatant liquid was decanted off and the resultant pellet was resuspended in 1 ml of a 0.2 μm filtered mixture containing 10 mM sodium acetate, 10 mM zinc acetate, pH 6.1, 40% PEG 8000 produced according to the method of Example 20. Using a spatula, the mixture was blended in a laminar flow hood to a uniform suspension containing 100 units/ml of crystalline insulin, and stored at 22° C. until used.

Example 28

Preparation of Crystalline human insulin suspension in 10 mM sodium until a uniform suspension containing 50×10$^6$ IU/ml of crystalline acetate, 10 mM zinc acetate, pH 6.1, 50% PEG 3350

Into a microcentrifuge tube was placed 1.0 ml of HUMULIN® U (Lilly) containing 100 units/ml of insulin and centrifuged in a Beckman microfuge II at 1000 rpm for 5 minutes. The supernatant liquid was decanted off and the resultant pellet was resuspended in 1 ml of a 0.2 μm filtered mixture containing 10 mM sodium acetate, 10 mM zinc acetate, pH 6.1, 50% PEG 3350 produced according to the method described in Example 21. Using a spatula, the mixture was blended in a laminar flow hood to a uniform suspension containing 100 units/ml of crystalline insulin, and stored at 22° C. until used.

Example 29

Preparation of Crystalline Bovine Insulin Suspension in 10 mM Sodium Acetate, 10 mM Zinc Acetate, pH 6.1, 40% PEG 8000

Into a microcentrifuge tube was placed 1.0 ml of ULTRALENTE® Insulin (Novo Nordisk) containing 100 units/ml of bovine insulin and centrifuged in a Beckman microfuge II at 1000 rpm for 5 minutes. The supernatant liquid was decanted off and the resultant pellet was resuspended in 1 ml of 0.2 μm filtered mixture containing 10 mM sodium acetate, 10 mM zinc acetate, pH 6.1, 40% PEG 8000 produced according to the method of Example 20. Using a spatula, the mixture was blended in a laminar flow hood to a uniform suspension containing 100 units/ml of crystalline insulin, and stored at 22° C. until used.

Example 30

Preparation of Crystalline Bovine Insulin Suspension in 10 mM Sodium Acetate, 10 mM Zinc Acetate, pH 6.1. 50% PEG 3350

Into a microcentrifuge tube was placed 1.0 ml of ULTRALENTE® Insulin (Novo Nordisk) containing 100 units/ml of bovine crystalline insulin and centrifuged in a Beckman microfuge II at 1000 rpm for 5 minutes. The supernatant liquid was decanted off and the resultant pellet was resuspended in 1 ml of 0.2 μm filtered mixture containing 10 mM sodium acetate, 10 mM zinc acetate, pH 6.1, 50% PEG 3350 prepared according to the method of Example 21. Using a spatula, the mixture was blended in a laminar flow hood to a uniform suspension containing 100 units/ml of crystalline insulin, and stored at 22° C. until used.

Example 31

Preparation of Crystalline Bovine Insulin Suspension in PEG 40,000/550 gel

Into a microcentrifuge tube was placed 1.0 ml of ULTRALENTE® Insulin (Novo Nordisk) containing 100 units/ml of bovine crystalline insulin and centrifuged in a Beckman microfuge II at 1000 rpm for 5 minutes. The supernatant liquid was decanted off and the resultant pellet was resuspended in 1 ml of 0.2 μm filtered mixture containing PEG 40,000/550 gel produced according to the method described in Example 22. Using a spatula, the mixture was blended in a laminar flow hood to a uniform suspension containing 100 units/ml of crystalline insulin, and stored at 22° C. until used.

Example 32

Preparation of Crystalline human Insulin suspension in PEG 40,000/550 gel

Into a microcentrifuge tube was placed 1.0 ml of HUMULIN® U (Lilly) containing 100 units/ml of crystalline insulin and centrifuged in a Beckman microfuge II at 1000 rpm for 5 minutes. The supernatant liquid was decanted off and the resultant pellet was resuspended in 1 ml of a 0.2 μm filtered mixture containing PEG 40,000/550 gel prepared according to the method described in Example 22. Using a spatula, the mixture was blended in a laminar flow hood to a uniform suspension containing 100 units/ml of crystalline insulin, and stored at 22° C. until used.

Example 33

Preparation of Crystalline human insulin suspension in PEG 3350/300 gel

Into a microcentrifuge tube was placed 1.0 ml of HUMULIN® U (Lilly) containing 100 units/ml of crystalline insulin and centrifuged in a Beckman microfuge II at 1000 rpm for 5 minutes. The supernatant liquid was decanted off and the resultant pellet was resuspended in 1 ml of a 0.2 μm filtered mixture containing PEG 3350/300 gel produced according to the method described in Example 23. Using a spatula, the mixture was blended in a laminar flow hood to a uniform suspension containing 100 units/ml of crystalline insulin, and stored at 22° C. until used.

Example 34

Preparation of Crystalline bovine insulin suspension in PEG 3350/300 gel

Into a microcentrifuge tube was placed 1.0 ml of ULTRALENTE® Insulin (Novo Nordisk) containing 100 units/ml of bovine crystalline insulin and centrifuged in a Beckman microfuge II at 1000 rpm for 5 minutes. The supernatant liquid was decanted off and the resultant pellet was resuspended in 1 ml of 0.2 μm filtered mixture containing PEG 3350/300 gel produced according to the method of Example 23. Using a spatula, the mixture was blended in a laminar flow hood to a uniform suspension containing 100 units/ml of crystalline insulin, and stored at 22° C. until used.

Example 35

Preparation of Crystalline human insulin suspension in PEG 3350/400 gel

Into a microcentrifuge tube was placed 1.0 ml of HUMULIN® U (Lilly) containing 100 units/ml of crystalline insulin and centrifuged in a Beckman microfuge II at 1000 rpm for 5 minutes. The supernatant liquid was decanted off and the resultant pellet was resuspended in 2 ml of a 0.2 μm filtered mixture containing PEG 3350/400 gel produced according to the method of Example 24. Using a spatula, the mixture was blended in a laminar flow hood to a uniform suspension containing 100 units/ml of crystalline insulin, and stored at 22° C. until used.

Example 36

Preparation of Crystalline Bovine Insulin Suspension in PEG 3350/400 gel

Into a microcentrifuge tube was placed 1.0 ml of ULTRALENTE® Insulin (Novo Nordisk) containing 100 units/ml of bovine crystalline insulin and centrifuged in a Beckman microfuge II at 1000 rpm for 5 minutes. The supernatant liquid was decanted off and the resultant pellet was resuspended in 1 ml of 0.2 μm filtered mixture containing PEG 3350/300 gel produced according to the method of Example 23. Using a spatula, the mixture was blended in a laminar flow hood to a uniform suspension containing 100 units/ml of crystalline insulin, and stored at 22° C. until used.

Example 37

Preparation of Crystalline Interferon alpha-2b Suspension in Sesame Oil

Into a microcentrifuge tube were placed 15 μl of crystalline zinc IFN-alpha-2b suspension containing $100\times10^6$ IU/ml of crystalline zinc IFN-alpha-2b and centrifuged in a Beckman microfuge II at 1000 rpm for 5 minutes. The supernatant liquid was decanted off and the resultant pellet was resuspended in 1 ml of 35 mM sodium acetate, 35 mM zinc acetate, pH 6.1. The suspension was centrifuged in a Beckman microfuge II at 1000 rpm for 5 minutes. The supernatant liquid was decanted off and the resulting pellet was resuspended in 2 ml of 0.2 μm filtered sesame oil (Spectrum). The resulting suspension was then vortexed on an orbital shaker until a uniform suspension containing $50\times10^6$ IU/ml of crystalline zinc IFN-alpha-2b in a sesame oil vehicle was obtained. This mixture was stored at 22° C. until it was used.

Example 38

Preparation of Crystalline Human Insulin Suspension in Sesame Oil

Into a microcentrifuge tube was placed 1.0 ml of HUMULIN® U (Lilly) containing 100 units/ml of crystalline insulin and centrifuged in a Beckman microfuge II at 1000 rpm for 5 minutes. The supernatant liquid was decanted off and the resultant pellet was resuspended in 1 ml of sesame oil (Spectrum) which had been filtered through a 0.2 μm filter resulting in a uniform suspension containing 100 units/ml of crystalline human insulin. This mixture was stored at 22° C. until used.

Example 39

Preparation of Crystalline Bovine Insulin Suspension in Sesame Oil

Into a microcentrifuge tube was placed 1.0 ml of ULTRALENTE® Insulin (Novo Nordisk) containing 100 units/ml of bovine crystalline insulin and centrifuged in a Beckman microfuge II at 1000 rpm for 5 minutes. The supernatant liquid was decanted off and the resultant pellet was resuspended in 1 ml of 0.2 μm filtered sesame oil (Spectrum) to a uniform suspension in a hood containing 100 units./ml. 4. Store at 22° C.

Example 40

Comparison of Protamine vs. PEG Vehicle

An in vivo study was set up to compare the controlled release properties of zinc-interferon suspensions in a protamine vehicle vs. a PEG based vehicle. Each of two Cynomolgus monkeys was injected in the small of the back with either the protamine vehicle containing crystalline zinc alpha interferon or with the PEG vehicle containing crystalline zinc alpha interferon. The alpha interferon in both the protamine vehicle and the PEG vehicle had come from the same batch preparation. The protamine/crystalline zinc alpha interferon was comprised of an aqueous solution of 10 mM sodium acetate, 10 mM zinc acetate, 0.4 mM protamine sulfate, pH 5.5 containing $50\times10^6$ International Units (IU) per dose. The PEG preparation was comprised of 10 mM sodium acetate, 10 mM zinc acetate, 40% PEG 8000, pH 5.5 also containing $50\times10^6$ IU per dose.

The interferon content in the blood serum of the monkeys was monitored at 0, 3.6, 24, 48, 72 and 96 hours. The interferon content in the monkey serum was measured by cytopathic effect inhibition (CPE) assay.

The virus which was used in the CPE assay was the Encephalomyocarditis virus (EMC), ATCC strain VR-129B, and was grown in monolayer cultures of Vero cells and stored frozen in Medium A. (Medium A is comprised of 950 ml of Minimum Essential Medium Eagle with Earle's balanced salt solution (Gibco Inc.), 100 ml fetal bovine serum, 36 ml of 7.5% sodium bicarbonate, 20 ml of 1M HEPES Buffer in saline, 20 ml of 200 mM L-Glutamine, and 10 ml of penicillin and streptomycin (10,000 unit of K-Penicillin/ml. and 10,000 μg streptomycin sulfate/ml). Confluent monolayers of FS-71 cells in tissue culture roller bottles were rinsed with Hank's balance salt solution and incubated at 37° C. for 10 minutes with a 2.5% trypsin solution. The trypsin solution containing the cells was diluted in Medium A such that the concentration of cells was $3.5\times10^5$ and used in the assay as described below.

Interferon Assay: The entire procedure for the anti-viral Bioassay was done in a 96 well microtiter plate. The samples to be tested were placed into the appropriate wells and serially diluted 1:2 across the plate. On each plate, 24 wells were filled with Medium A to serve as virus and cell controls. Additionally, a laboratory standard of interferon alpha-2b containing 600 IU/ml of Interferon alpha-2b was diluted to 1 IU/ml, the concentration level necessary to give a 50% protection level from viral cytopathology, was included in all assays so that the relative anti-viral activity of samples could be determined and compared across assays.

Each well was then seeded with approximately $3.5\times10^4$ cells in 0.1 ml of Medium A. The plate was covered and incubated at 37° C., 5% $CO_2$ for 4 hours. All wells, except the cell control wells, received EMC virus at a concentration appropriate to induce 90–100% cytopathology in 16–18 hours post-infection which was approximately $1.54\times10^4$ plaque forming units. The plates were recovered and incubated at 37° C., 5% $CO_2$ until the virus control wells displayed a cytopathic effect (CPE) of at least 90%. The media from each well was aspirated and the cell monolayer was strained with 0.1 ml crystal violet preparation for about 30 minutes. After the crystal violet was decanted, the plates were gently rinsed with water and allowed to air dry. The virus and cell control wells were scored from 1 to 4+ (1=<10% CPE and 4+=>90% CPE) by visual inspection of the monolayer with and without a microscope. Samples on test plates that showed appropriate control responses were then graded.

The grading of each sample well consisted of visual examination and comparison by the standard wells. The 50% endpoint for samples are determined by direct comparison to the 50% endpoint for the standard by selection of the sample well(s) which match most closely. The shift in a sample's 50% endpoint as compared to that of the standard gives estimates of titer values relative to the standard. Therefore, a shift of X wells [X=(50% well No. for sample)−(50% well No. for standard)] translates to a potency of $2^x$ times the potency of the standard. A detailed description of the assay is provided in S. Rubinstein, P. C. Familetti and S. Petska, *J. Virol.* 37:755 (1981).

The data are shown in FIG. 2. The mean interferon levels (IU/ml) in monkey serum were plotted against time. The dotted line on the graph indicates the serum level of interferon in the monkey which was administered crystalline zinc alpha interferon in the protamine vehicle; while the solid line indicates the serum level of alpha interferon in the monkey which was administered crystalline zinc alpha interferon in a PEG vehicle.

The data from the present study strongly suggests that the PEG formulation enhances the controlled release effect of the crystalline protein. This effect can be demonstrated by examination of the pharmacokinetic profile shown in Table 2. A visual estimate of the area under the curve (AUC) for immediate release interferon and the crystalline suspension in the PEG solution is shown in FIG. 3. Also, note the difference in the shape of the curve for the immediate release vs. crystalline IFN preparations. Rather than the "burst" phenomenon observed in the immediate release preparation, there is a lower level of IFN available systemically over a prolonged period of time in the crystalline IFN preparation.

TABLE 3

Range of Components Tested

| PEG | Formulation Buffers | pH | Temp (° C.) | Crystalline Suspension |
|---|---|---|---|---|
| 8000 | 40% soln sodium/ zinc acetate | 6.0–6.1 | 4–37 | human IFN, bovine insulin, human insulin |
| 3350 | 50% soln sodium/ zinc acetate | 6.0–6.1 | 4–37 | human IFN, bovine insulin, human insulin |
| 40,000/550 | gel | — | 4–37 | human IFN, bovine insulin, human insulin |
| 3359/400 | gel | — | 4–37 | human IFN, bovine insulin, human n insulin |
| 3359/300 | gel | — | 4–37 | human IFN, bovine |

TABLE 4

MEAN SERUM LEVEL (CPE)

| Time (hr) | IFN α-2b | Crys/Prot-1 | Crys/Prot-2 | PEG |
|---|---|---|---|---|
| 0 | 0 | 0 | 0 | 0 |
| 1 | 0 | 676 | 594 | 24 |
| 3 | 8000 | 1500 | 880 | 784 |
| 6 | 150 | 900 | 643 | 795 |
| 10 | 0 | 900 | ND | ND |
| 24 | 0 | 114 | 2 | 501 |
| 48 | 0 | 0 | 0 | 22 |
| 72 | 0 | 0 | 0 | 2 |

Example 41

Vegetable Oil Gel Formulation

INGREDIENTS

| Crystalline zinc IFN alpha-2b | 10–1000 mcg |
| Vegetable oil for emulsion | 2 ml |
| Vegetable oil for gel | 2 ml |
| Aluminum monostearate | 50 mg |

To prepare the controlled release preparation of crystalline zinc IFN alpha-2b, the aluminum monostearate is mixed into the vegetable oil for the gel and heat elevated to form the gel according to known methods.

The crystalline zinc IFN alpha-2b is placed into the peanut oil for emulsion and mixed by vortexing. The resultant emulsion is then mixed into the previously prepared gelled vegetable oil and mixed by vortexing. Preferred vegetable oils are peanut, saffron, sesame and canola oils.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

What is claimed is:

1. An injectable sustained release pharmaceutical composition comprised of a mixture of a crystalline alpha interferon and polyethylene glycol (PEG).

2. The pharmaceutical composition of claim 1 wherein the PEG is selected from the group consisting of PEG 8000, and PEG 3350.

3. The pharmaceutical composition of claim 1 wherein the polyethylene glycol is a mixture of polyethylene glycols of varying molecular weights.

4. The pharmaceutical composition of claim 3 wherein the PEG is a mixture of PEG 3350 and PEG 400.

5. The pharmaceutical composition of claim 3 wherein the PEG is a mixture of PEG 40,000 and PEG 550.

6. The pharmaceutical composition of claim 1 wherein the crystalline interferon-alpha is a crystalline interferon alpha 2-b.

7. The pharmaceutical composition of claim 1 wherein the crystalline interferon-alpha is a zinc crystalline interferon alpha.

8. The pharmaceutical composition of claim 7 wherein the zinc crystalline interferon-alpha is a zinc crystalline interferon-alpha-2b.

9. A method for producing a pharmaceutical composition according to claim 1 comprising mixing a crystalline interferon-alpha with polyethylene glycol.

10. The method of claim 9 wherein the PEG is selected from the group consisting of PEG 8000, and PEG 3350.

11. The method of claim 9 wherein the polyethylene glycol is a mixture of polyethylene glycols of varying molecular weights.

12. The method of claim 11 wherein the PEG is a mixture of PEG 3350 and PEG 400.

13. The method of claim 12 wherein-the PEG is a mixture of PEG 40,000 and PEG 550.

14. An injectable sustained-release pharmaceutical composition comprised of a mixture of a crystalline interferon-alpha and a pharmaceutically acceptable vegetable oil.

15. The pharmaceutical composition of claim 14 wherein the vegetable oil is selected from the group consisting of peanut oil, sesame oil, saffron oil and canola oil.

16. A method for administering a crystalline interferon-alpha to an individual comprising placing crystalline interferon alpha in a polyethlene glycol (PEG) vehicle; and injecting the PEG vehicle containing crystalline interferon-alpha into the individual.

17. The method of claim 16 wherein the PEG is selected from the group consisting of PEG 8000, and PEG 3350.

18. The method of claim 16 wherein the polyethylene glycol is a mixture of polyethylene glycols of varying molecular weights.

19. The method of claim 18 wherein the PEG is a mixture of PEG 3350 and PEG 400.

20. The method of claim 18 wherein the PEG is a mixture of PEG 40,000 and PEG 550.

21. A method for administering a crystalline interferon-alpha to an individual comprising placing crystalline interferon-alpha in a sesame oil vehicle; and injecting the sesame oil vehicle containing crystalline interferon-alpha into the individual.

22. A method for producing a pharmaceutical composition comprising mixing a pharmaceutically acceptable vegetable oil with a crystalline interferon-alpha.

23. The method of claim 22 wherein the vegetable oil is selected from the group consisting of peanut oil, sesame oil, saffron oil and canola oil.

* * * * *